(12) United States Patent
Aramli

(10) Patent No.: US 9,907,407 B2
(45) Date of Patent: Mar. 6, 2018

(54) BLANKET APPARATUS FOR DISTRIBUTING CONDITIONED AIR INTO ZONES OF A BED

(71) Applicant: Mark Darius Aramli, Newport, RI (US)

(72) Inventor: Mark Darius Aramli, Newport, RI (US)

( * ) Notice: Subject to any disclaimer, the term of this patent is extended or adjusted under 35 U.S.C. 154(b) by 0 days.

(21) Appl. No.: 15/441,217

(22) Filed: Feb. 23, 2017

(65) Prior Publication Data

US 2017/0164758 A1 Jun. 15, 2017

Related U.S. Application Data

(63) Continuation-in-part of application No. 14/276,162, filed on May 13, 2014, now abandoned.

(51) Int. Cl.
*A47C 21/04* (2006.01)
*A47G 9/02* (2006.01)
(Continued)

(52) U.S. Cl.
CPC ............ *A47C 21/044* (2013.01); *A47C 21/04* (2013.01); *A47C 21/042* (2013.01); *A47C 21/048* (2013.01); *A47G 9/0215* (2013.01); *A47G 9/0223* (2013.01); *A61F 7/00* (2013.01); *A47G 2009/003* (2013.01)

(58) Field of Classification Search
CPC ... A47C 21/044; A47C 21/042; A47C 21/048; A47G 9/0223; A47G 2009/003; A47G 9/02; A47G 9/023; A61G 7/05784; A61G 7/05792
See application file for complete search history.

(56) References Cited

U.S. PATENT DOCUMENTS 4,660,388 A * 4/1987 Greene, Jr. .......... A47G 9/0215
165/46
4,777,802 A * 10/1988 Feher .................. A47G 9/0215
5/423
(Continued)

FOREIGN PATENT DOCUMENTS

CA           2295584 C      7/2005

*Primary Examiner* — Nicholas F Polito
*Assistant Examiner* — Rahib T Zamna
(74) *Attorney, Agent, or Firm* — Robert J. Hess; Hess Patent Law Firm

(57) ABSTRACT

A bed covering or blanket apparatus for accepting and distributing a pressurized flow of conditioned air into a zone around the body of a bed occupant. The apparatus includes an upper layer and lower layer of differing air permeability, joined to form a flow cavity between them for the pressurized air. A plurality of joining methods between the upper and lower layer is provided within the flow area to prevent the blanket from ballooning under the pressurized airflow. The bed covering or blanket apparatus contains means to cover an entire bed while directing pressurized conditioned air to specific zones of the bed. There is connection of two independent supplies of conditioned air into a single top layer of bedding under which multiple bed occupants sleep, to evenly distribute such independent supplies into specific dual zone areas. The apparatus achieves its function by utilizing materials that are ordinarily used in existing bed linens and comforters.

30 Claims, 12 Drawing Sheets

(51) Int. Cl.
*A61F 7/00* (2006.01)
*A47G 9/00* (2006.01)

(56) References Cited

U.S. PATENT DOCUMENTS

| | | | | |
|---|---|---|---|---|
| 5,265,599 A * | 11/1993 | Stephenson | ............ | A61F 7/0097 165/46 |
| 5,304,213 A * | 4/1994 | Berke | .................. | A47G 9/0215 607/104 |
| 5,384,924 A * | 1/1995 | Dickerhoff | ........... | A47G 9/0215 5/421 |
| 5,405,371 A * | 4/1995 | Augustine | ............ | A47G 9/0215 607/107 |
| 6,119,474 A * | 9/2000 | Augustine | ............ | A47G 9/0215 607/107 |
| 6,168,612 B1 * | 1/2001 | Augustine | ............ | A47G 9/0215 601/16 |
| 6,363,551 B1 * | 4/2002 | Flores | .................. | A47C 21/044 5/421 |
| 7,631,377 B1 * | 12/2009 | Sanford | ................ | A47C 21/044 5/413 R |
| 2003/0145380 A1 * | 8/2003 | Schmid | ................ | A47C 21/044 5/423 |
| 2010/0235991 A1 * | 9/2010 | Ward | .................... | A47C 21/044 5/423 |
| 2011/0289684 A1 * | 12/2011 | Parish | .................. | A47C 21/044 5/421 |
| 2012/0017371 A1 * | 1/2012 | Pollard | ................ | A47G 9/0215 5/423 |
| 2014/0182061 A1 * | 7/2014 | Zaiss | .................... | A47C 21/044 5/423 |
| 2015/0074904 A1 * | 3/2015 | Aramli | ................. | A47C 21/042 5/421 |
| 2015/0231009 A1 | 8/2015 | Lewis | | |

\* cited by examiner

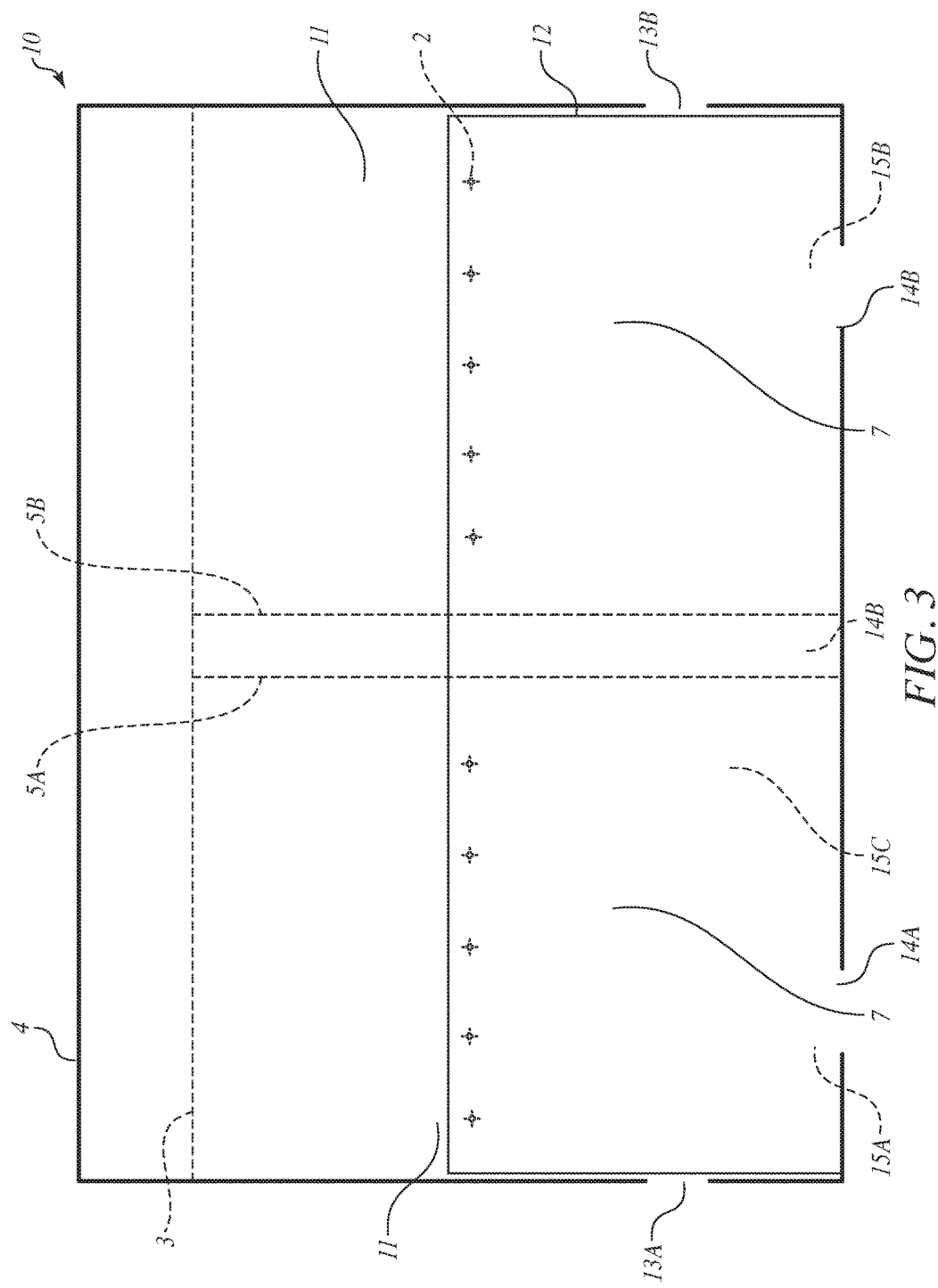

BLANKET APPARATUS FOR DISTRIBUTING CONDITIONED AIR INTO ZONES OF A BED

REFERENCE TO COPENDING PATENT APPLICATIONS

The present application is a continuation-in-part of application Ser. No. 14/276,162 that was filed May 13, 2014.

BACKGROUND OF THE INVENTION

The invention relates to a blanket apparatus for distribution of a flow of pressurized conditioned air into a zone around the body of a bed occupant. More specifically, the invention relates to an engineered layer of bedding that connects to a supply of pressurized conditioned air that evenly distributes such conditioned air to a single specific zone of the bed. The invention additionally contemplates connection of two independent supplies of conditioned air into the single layer of engineered bedding to evenly distribute such independent supplies into specific dual zone areas about the multiple bed occupants, thus providing independently conditioned zones within the bed for each occupant. The invention further avoids the feeling of foreign and unnatural apparatus in the bed to the occupants by providing for a bedding texture against the skin of ordinary cotton linens and comforters.

The body of the average person releases a substantial amount of heat through skin loss and moisture due to perspiration to the surrounding air. The usual practice of covering the body during sleeping has the effect of insulating the body from the surrounding room air and thereby holds such released heat and moisture in the air about the body.

In cold weather when the room temperature may be below 70 F. heavy covering is frequently employed so as to minimize the exchange of air about the body with the surrounding room air and thus has the effect of increasing the air temperature and humidity about the body. In such instances a person will often throw off the covering while asleep, which will then result in chilling.

In warm weather when the room temperature is above 70 F., a lighter covering is usually employed but the moisture which results from perspiration is still retained about the body by the insulating covering, causing personal discomfort and results in poor rest.

The obese and the bedridden are particularly troubled by these conditions of the air environment about the body. Many home and hospital patients have body temperature conditions which ideally require controlled surrounding air and humidity conditions within the bed environment.

Room air conditioners which have heretofore been provided for regulating the room air temperature and humidity conditions have the disadvantages of handling large volumes of air, requiring special electrical power, and are relatively expensive for installation, operation and maintenance costs. Even with room air conditioners, the person usually employs some form of covering which insulates the body from the surrounding air so there remains no suitable means of exchanging the air between the body and the covering of the occupant's bed.

There are a many causes of the various known sleep disorders. Of these causes the physical comfort of the person attempting to sleep or rest is paramount, for if a person's ambient surroundings are not conducive to their personal comfort, sleep can become extremely difficult to achieve, if at all. One factor in the person's environment that has a bearing on their ability to achieve sleep is the ambient temperature. If the temperature of the surroundings of a person is either too hot or too cold, restful sleep may be impossible. Of particular concern is the case where the surroundings are too hot, because in such cases the body's ability to control its internal temperature may be effected to the point where the body begins to sweat, and it is nearly impossible to achieve restful sleep while sweating. Thus, maintaining the ambient temperature at a level which is conducive to sleep is a key to enabling a person to sleep.

Means for controlling the ambient temperature in a person's surroundings are known to include the provision of "air conditioning" in which an air conditioner utilizing the principles of Joule-Thomson cooling is employed to extract heat from a volume of air, such as a bedroom. While air conditioners are highly effective at coarsely controlling the temperature in a room, the customary preference for persons to sleep beneath one or more bed sheets, covers, blankets, etc., coupled with the body's tendency to liberate heat during its normal operation translates to the well-known situation in which the person resting beneath the sheets cannot get comfortable because they are too hot, which is compounded by the proposition that if they remove the covers or sheets from themselves then they become too cold.

Owing to variance between selected individual human subjects' metabolism, genetics, etc. the method used in the fine tuning control of one's body temperature becomes a matter of personal taste or preference, and many individuals have typically been observed to develop their own personal habits of effecting such fine tuning, such as sleeping with more or less clothing, permitting part of the body to be exposed to the open air, etc. It is a common observation that two individuals sharing a bed may have widely different requirements of hot and cold within the ambient air of the bedding for comfortable sleep.

In spite of these efforts, however, perfect control of the temperature of ambient surroundings of persons in a bed desiring to sleep has been fleeting, with particular difficulty for partners who share a bed with different sleep temperature preferences. This fact is evidenced by the myriad of schemes and contrivances provided by workers in the prior art for effecting thermal control over a bed or region in which a person normally rests for sleep utilizing a pressurized flow of air, the following few of which are exemplary, and are herein incorporated by reference in their entirety.

While there are conventional devices and methods that achieve to a greater or less extent their desired objectives, they are nevertheless lacking features which have heretofore prevented their widespread adoption by large numbers of people. They fail to provide a bedding apparatus that can evenly distribute a pressurized flow of air through a bed into both one or two independent zones, while not causing ballooning of bedding due to flow of air. Moreover, there are conventional devices and methods that introduce either foreign textures or objects to the user in the bed, which is a highly undesirable feature.

Thus, there exists a need for an improved system for distributing both warm and ventilated or cool conditioned air throughout a bed into one or two zones, while not introducing elements or textures to the users that were previously foreign to the bed, while also avoiding giving rise to a ballooning effect of the bedding while delivering the pressurized air.

BRIEF SUMMARY OF THE INVENTION

The foregoing and other problems are overcome, and other advantages are realized, in accordance with the presently preferred embodiments of these teachings.

One aspect of the invention provides a top bedding blanket assembly interconnected with an external apparatus which supplies a pressurized flow of conditioned air, such that the air can be evenly distributed within a zone of a bed and not provide the feeling of "rushing air" to the occupants.

Another aspect is the provision of a top bedding blanket assembly accepting two independent flows of conditioned air from external apparatus for even distribution into two independent zones within the bed, thus accommodating two occupants' different bed temperature preferences while simultaneously allowing a single top bedding blanket apparatus to cover both occupants without separation between the occupants.

Yet another aspect of the invention is the provision of accepting both heated, ambient and cooled air as a means of establishing multiple zones of temperature within a bed Yet another aspect of the invention is to avoid introducing foreign textures or surfaces in contact with the bed occupants other than those that are already commonly used in existing residential bedding such as cotton, cotton blends, and synthetic microfiber materials.

A further aspect of the invention is to allow for sufficiently pressurized airflow into the blanket apparatus to evenly distribute air without a large ballooning effect of the blanket or bedding In accordance with one embodiment of the invention is a lower layer sheet comprised of a cotton, cotton blend, or synthetic microfiber, or other similar material commonly used in residential bedding that has some permeability to air, that is joined to an upper layer sheet of similar material but of tighter weave with a lower natural permeability to air. The joining of the two layers, such as with thread stitches, thus creates an interior space for the flow of air. The upper layer is arranged in a major surface area contacting relation with the lower layer. The joining is preferably arranged in a substantially continuous closed path with allowance for an inlet port for pressurized conditioned air. The lower layer sheet and upper layer sheet are preferably joined by a plurality of joining methods within the air flow area that enables contiguous connection to the air flow stream while preventing ballooning of the blanket apparatus while under natural pressure from the flow of pressurized air.

A differential in air permeability can be used advantageously to promote airflow to desired regions of bedding. For instance, layers that are joined together to form regions of lower air permeability and regions of higher air permeability can be sized to promote a desired effect to promote airflow, because the airflow tends to migrate toward the regions of higher air permeability and away from regions of lower air permeability.

In accordance with the invention, therefore, it is preferable to have regions of bed covering that is further way from the foot of the bed (when the bed covering is laid upon a bed) to have higher air permeability than the region closer to the foot of the bed where air inlets are provided to allow for entry of forced air into the bed covering. One way to accomplish this result is to add a layer of woven material to the region of the bed covering that is closer to the foot of the bed that does not extent to the region of the bed covering that is closer to the head of the bed when the bed covering is laid out over a bed. Another way is to may the weave of the region closer to the head of the bed less tight or dense that the region closer to the foot of the bed.

With respect to lower and upper layers of the bed covering (between which airflow is introduced), it is preferably to make the upper layer less air permeable than the lower so as to promote substantially more of the airflow to be directed toward the occupants who are beneath the lower layer in the bed. Doing so also has the added advantage of avoiding the need for an unsightly appearance from arising because of the presence of any holes, apertures or other venting means or textures in the lower and upper layers which would not normally be present in conventional bedding sheets or comforters. If both of the upper and lower layers are permeable to air, such a condition increases the occupants' comfort to a more natural bedding experience during times when pressurized air is not supplied.

In accordance with another embodiment of the invention another feature of the apparatus is a limited flow zone area, where the pressurized conditioned air is directed to only half or some portion of a bed, while the blanket apparatus still covers the entire bed area. As an another option, a dual zone flow area, is provided for which one flow area is sealed from the other and both have independent inlets for pressurized conditioned air, thus creating a two zone conditioning system for the bed.

In accordance with yet another embodiment of the invention, multiple inlets in different locations are provided to accommodate different style beds. For example beds with footboards may not be easy to plug the air supply in at the foot of the bed. By providing for multiple locations for the inlet ports to accommodate different beds, the air supply may be plugged in from either of the sides or from the foot of the bed. The inlet ports are sealable if not used.

BRIEF DESCRIPTION OF THE DRAWINGS

For a better understanding of the present invention, reference is made to the following description and accompanying drawings, while the scope of the invention is set forth in the appended claims.

FIG. 3 is a schematic diagram of an interior view of an internal layer of the dual zone embodiment in accordance with the dual zone embodiment of FIG. 2.

DETAILED DESCRIPTION OF THE PREFERRED EMBODIMENT

Figure 1:
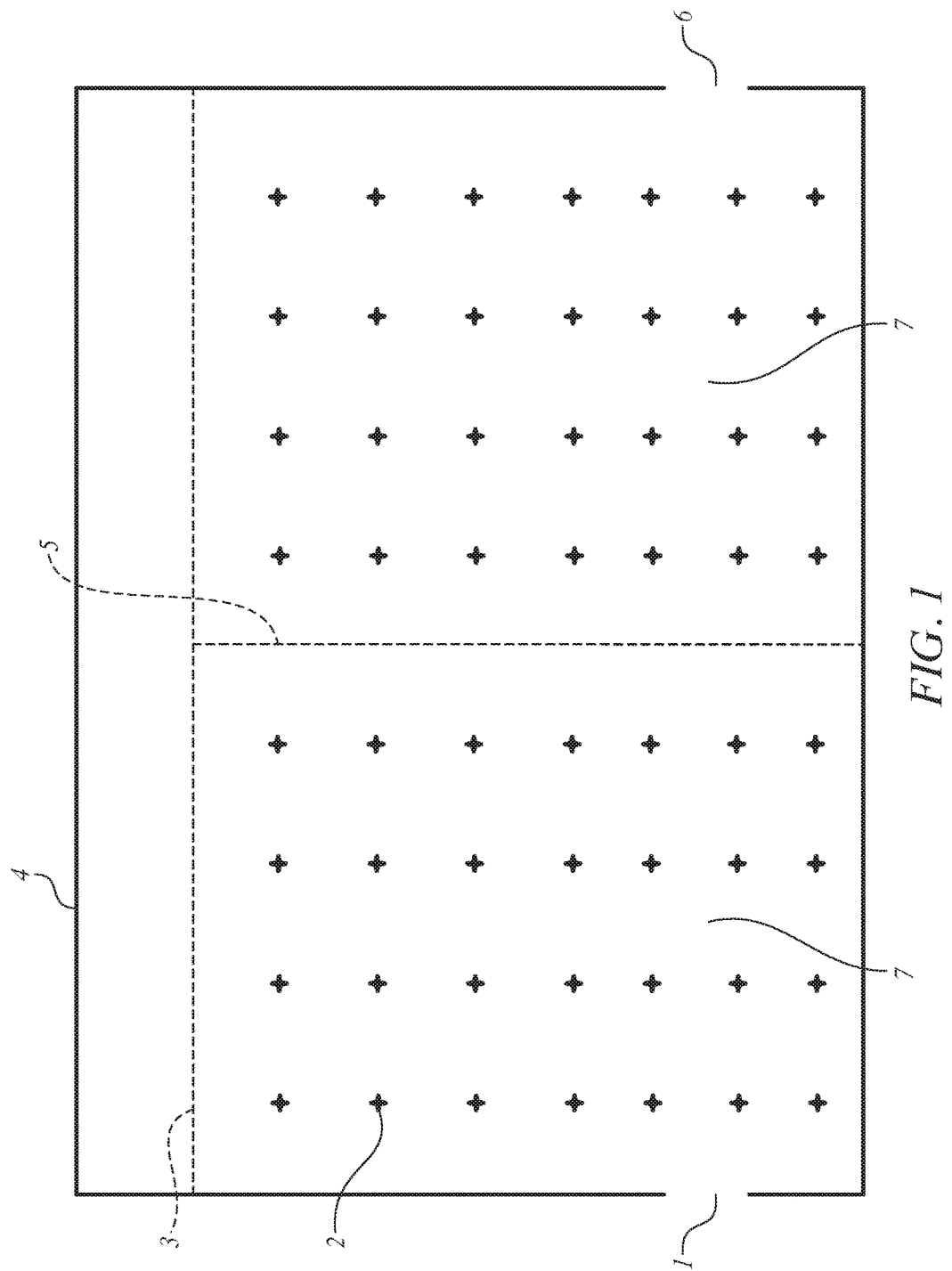
FIG. 1 is a schematic diagram of an exterior view of a blanket in accordance with an embodiment of the invention that distributes conditioned air into zones of a bed.

Referring now to FIG. 1, there is shown a pictorial illustration of a bed covering in accordance with the invention. There is an unsealed area 1 between upper and lower sheets where a pressurized airflow can be supplied by a hose or other means into the flow area. However, there is a sealed edge 4 between the upper and lower layer sheets. As a consequence of the sealed edge 4, the sealed upper and lower sheets form a flow area 7. A thermal layer may be sewn onto either of the upper and lower sheets to provide a greater thermal insulating characteristic to the bed covering than from just the upper and lower sheets. In so doing, the bed covering can be considered to be a blanket.

There are plurality of thread stitches 2 between the upper and lower layer sheets allows open flow paths, but prevents a ballooning effect of the joined sheets from arising when under pressurized airflow. Such a ballooning effect is avoided in accordance with the construction of the bed covering or blanket in accordance with the invention because of the placement of the thread stitches 2 in a uniform manner in the central region of the bed covering or blanket. Instead of the thread stitches 2, glue or mechanical fasteners or any form of joining means may be used to join together the upper and lower sheets. The thread stitches 2 may be tack stitches.

An optional sealing line 3 between the upper and lower layers may be provided to further distinguish a smaller zone in the bed that will not need to be inflated. An additional optional sealing line 5 between the upper and lower layers may be provided to create an independent dual zone flow area. The sealing lines 3, 5 may be in the form of a sealing mechanism such as a conventional hook and loop fastener strip that fastens the hooks and loops to each other in a releasable manner, or ordinary thread stitching An additional unsealed area 6 between the upper and lower sheets may be provided for a second independent conditioned flow of air to support the dual zone airflow nature of the apparatus. The unsealed areas 1, 6 constitute ports or access areas for accommodating insertion of ends of air hoses that discharge pressurized conditioned air from a source into the flow area 7.

Figure 2:
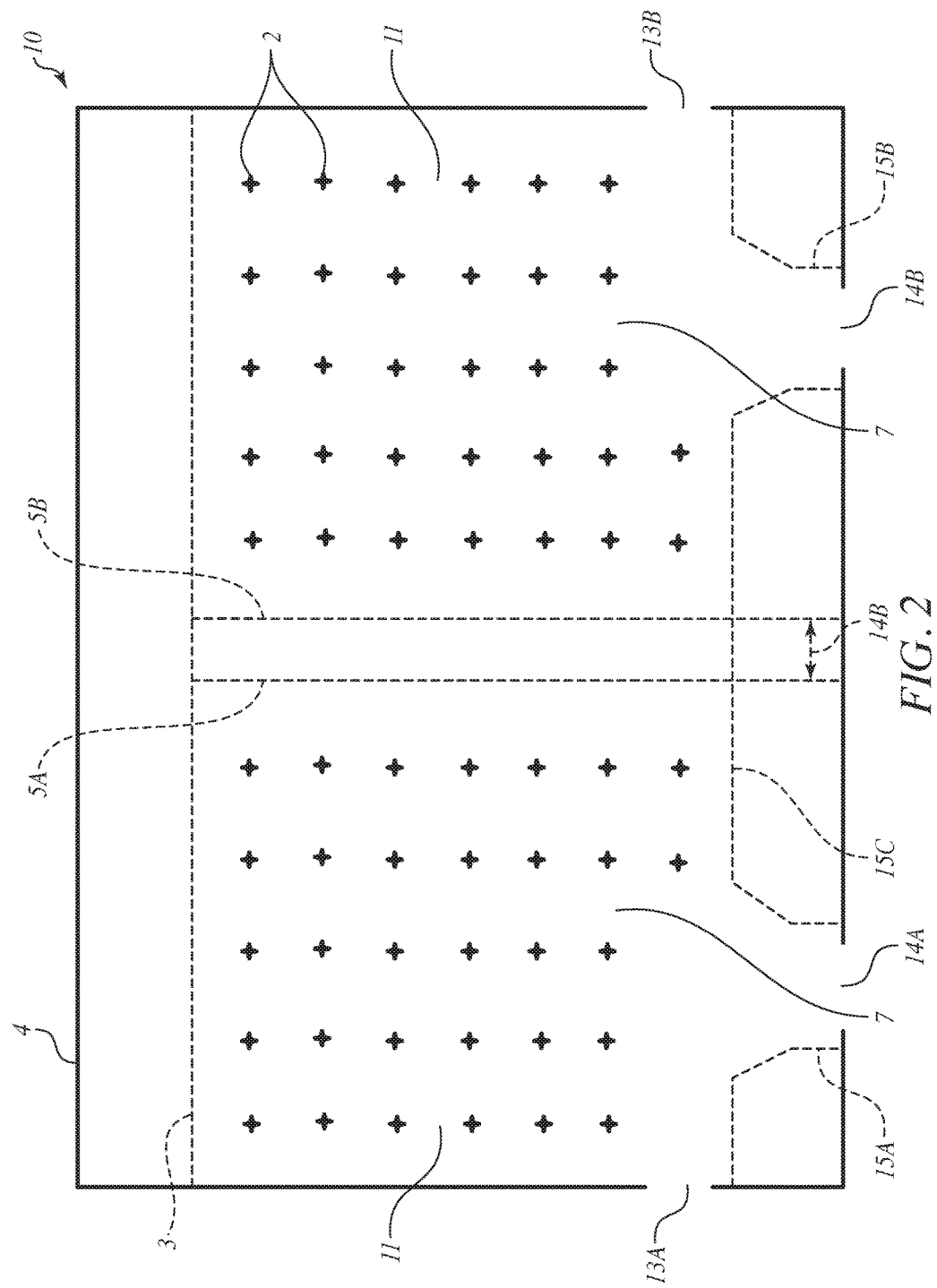
FIG. 2 is a schematic diagram of an exterior view of an uninflated blanket in accordance with a dual zone embodiment of the invention that distributes conditioned air into zones of a bed.
Figure 3A:
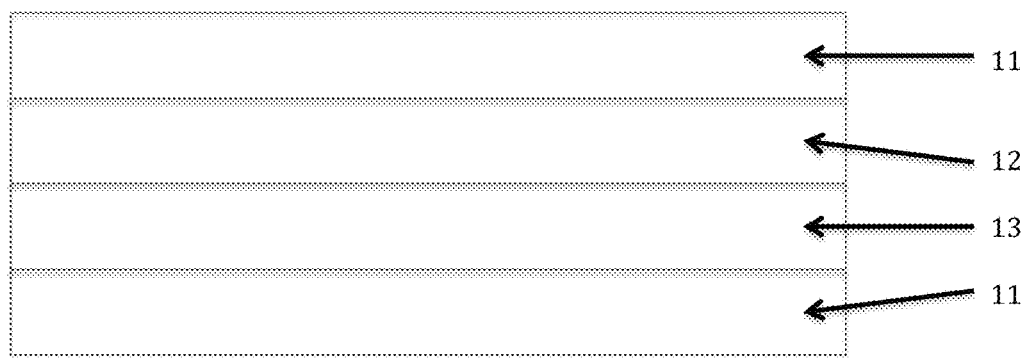
FIG. 3A is a schematic diagram showing and end view of layers of the bed covering stacked one over another.
Figure 4:
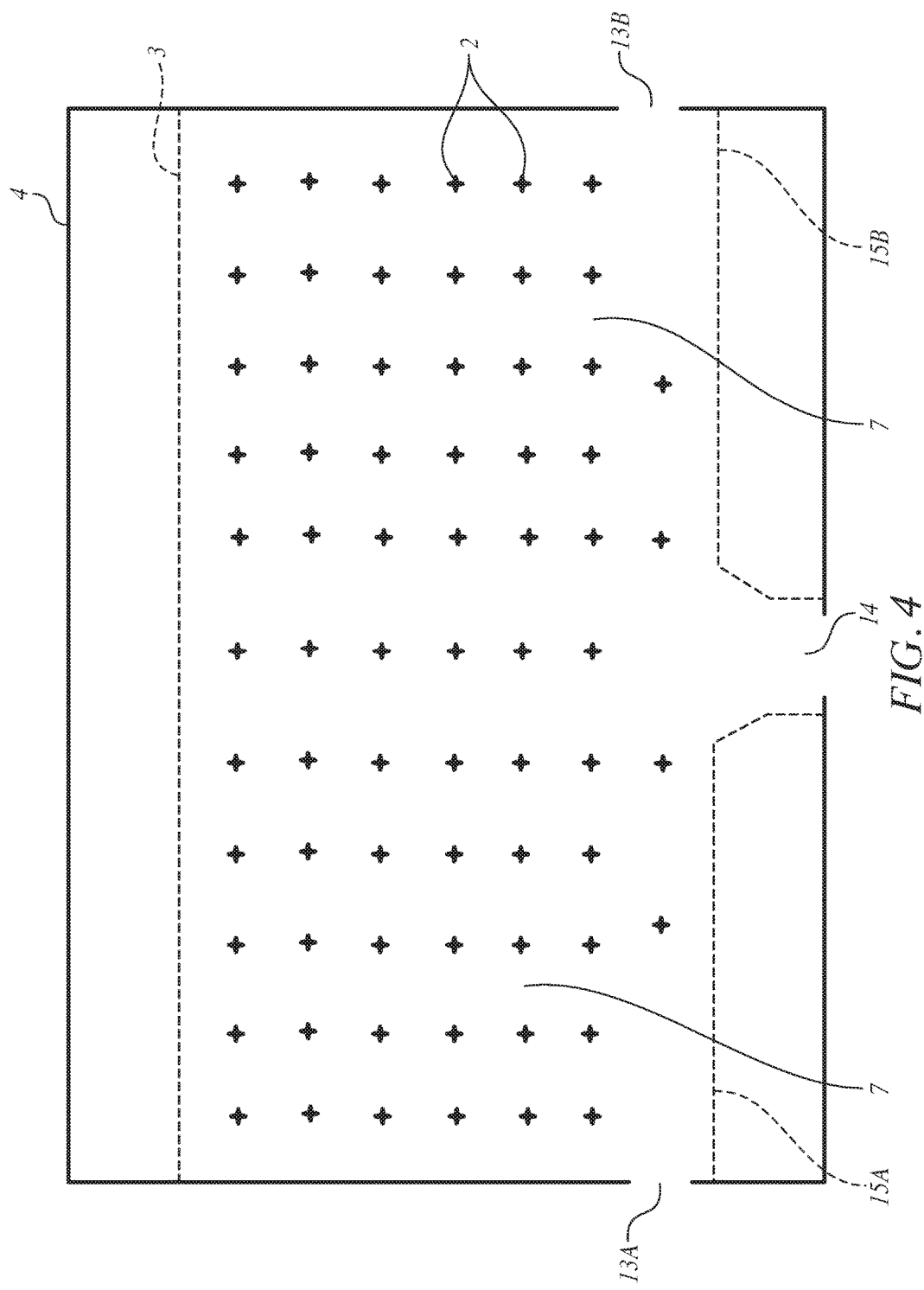
FIG. 4 is a schematic diagram of an exterior view of a non-inflated blanket in accordance with a single zone embodiment of the invention that distributes conditioned air into zones of a bed.
Figure 5:
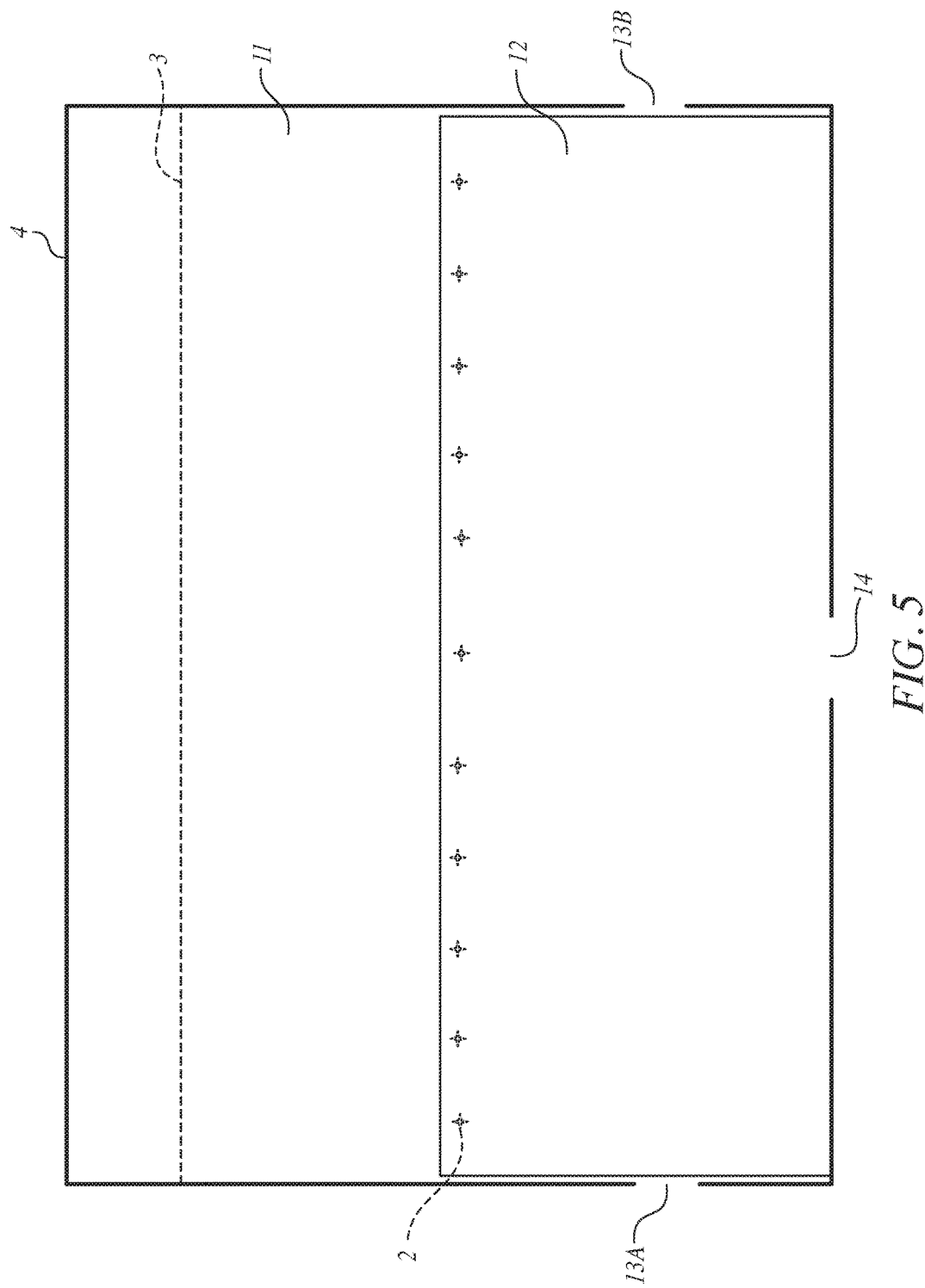
FIG. 5 is a schematic diagram of an interior view of an internal layer of the single embodiment in accordance with the single zone embodiment of FIG. 4.

Turning to the dual zone embodiment of FIGS. 2 and 3 and the single zone embodiment of FIGS. 4 and 5, the bed covering or blanket 10 has upper and lower sheet layers 11 with an interior (or middle) layer 12 between and optionally a thermal layer 13 (as shown in FIG. 3A) sewn to one of the upper or lower sheet layers 11 to provide a higher thermal insulating characteristic than is afforded just by the upper and lower sheet layers 11 and the interior layer 12. The interior layer 12 is shorter than the upper and lower sheet layers 11 and may be sewn onto a bottom portion and topside of the lower one of the sheet layers 11 to form a double layer section. This double layer section serves to create two different zones of air permeability to force more air to exit towards the top of the sheet. The interior layer 12 is also preferably sewn to side and bottom sheet seams and may be anchored to a row of tack stitches 2 at the locations indicated in FIGS. 3 and 5. As an alternative and not shown in the drawings, the interior layer 12 could be sewn instead to the bottom portion and underside of the upper sheet layer 11.

The upper one of the sheet layers 11 is preferably a downproof sateen and the lower one of the sheet layers 11 as well as the interior layer 12 are preferably of percale. The lower one of the sheet layers 11 is more air permeable than the upper one of the sheet layers 11. The upper portion of the lower sheet layer is more air permeable than the lower portion of the lower sheet layer due to the double layer. As a result, blowing air into the flow area 7 between the upper and lower sheet layers 11 will result in most of the blown air permeating through upper regions of lower sheet layer 11 that are away from the lower regions where the interior layer 12 is present.

There are two sealing lines 5A, 5B in FIGS. 2 and 3 that extend centrally from an optional sealing line 3 to the bottom edge of the upper and lower sheets 11. The sealing lines 3, 5A, 5B may be in the form of a stitching thread or a conventional hook and loop fastener strip that fastens the hooks and loops to each other in a releasable manner. Thus, one may convert the bed covering or blanket 10 of FIGS. 2 and 3 having dual zones into one having a single zone in the manner of that of FIGS. 4 and 5, except there would still be the two openings 14A, 14B at the bottom as in FIGS. 2 and 3 as opposed to just a single bottom opening 14 as in FIGS. 4 and 5.

Additional sealing lines 15A, 15B are provided that extend from the bottom edge of each of the side openings 13A, 13B in a direction inwardly and then turn to run adjacent to respective sides of the bottom openings 14A, 14B. In addition, there is an additional sealing line 15C that run from the remaining sides of the bottom openings 14A, 14B inwardly and the across as shown. The purpose is to shrink the total flow area of the sheet system to only those areas of the bed where flow is desired.

In the case of the bed covering or blanket 10 being for king size, there are five tack stitches per row on each side joining top and bottom layers, evenly spaced apart from each other starting at the center seam. In the case of the bed covering or blanket 10 being for a queen size, there are four tack stitches per row on each side instead of five. In the case of the bed covering or blanket 10 being for double size, there may be three track stitches per row on each side instead of four for the queen size and instead of five for the king size.

Since the dual zone embodiment of FIGS. 2 and 3 has dual zones, each of the zones is provided with its own set of side and bottom openings 13A, 13B, and 14A, 14B. Since the single zone embodiment of FIGS. 4 and 5 has a single zone, there are side openings 13A, 13B, but only a single centrally located bottom opening 14. Multiple inlet openings are provided into the same flow area to provide flexibility to the user to determine air inlet location most suitable to their bed setup or preference.

The flow areas 7 throughout the bed covering or blanket 10 become inflated around the thread stitches 2. Even though the bottom portion of the bed covering or blanket 10 lacks tack stitches 2, the enhanced reduction in air permeability afforded by the interior layer 12 in effect causes the air to flow or migrate under pressure to the portion of exterior layer 11 that has greater air permeability. The net effect is to allow inlet of air from the lower portion of the bed covering where the feet would commonly be located, and to have much of this air bypassed to the area of the bed covering where the torso would be located.

In the case of the single zone embodiment of FIGS. 4 and 5, the number of tack stitches per row on each "side" is the same as for the dual zone embodiment of FIGS. 2 and 3, except there is an additional tack stitch provided at the center between the two "sides", where arises the central divider space 15 for the dual zone embodiment of FIGS. 2 and 3. Also, the sealing lines 15A, 15B each extend from respective areas adjacent the lower sides of the side openings 13A, 13B inwardly until turning to run adjacent respective sides of the single centrally located bottom opening 14. The sealing lines 15A, 15B (FIGS. 2 and 4) and the sealing line 15C (FIG. 2) may each in the form of common thread stitching.

Figure 6:
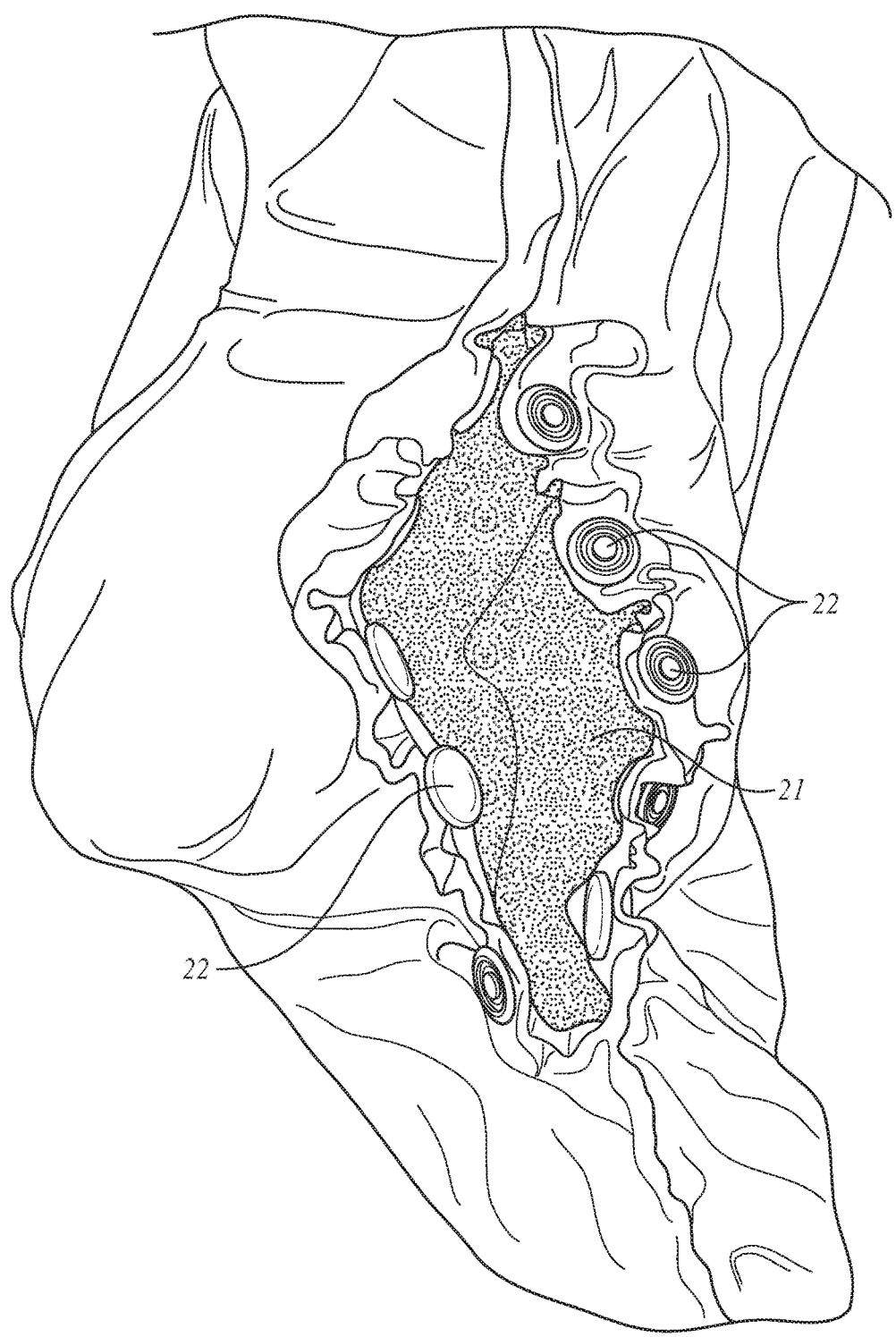
FIG. 6 is an isometric view of a hose seal in an open position accordance with the invention to show snaps about an opening.
Figure 7:
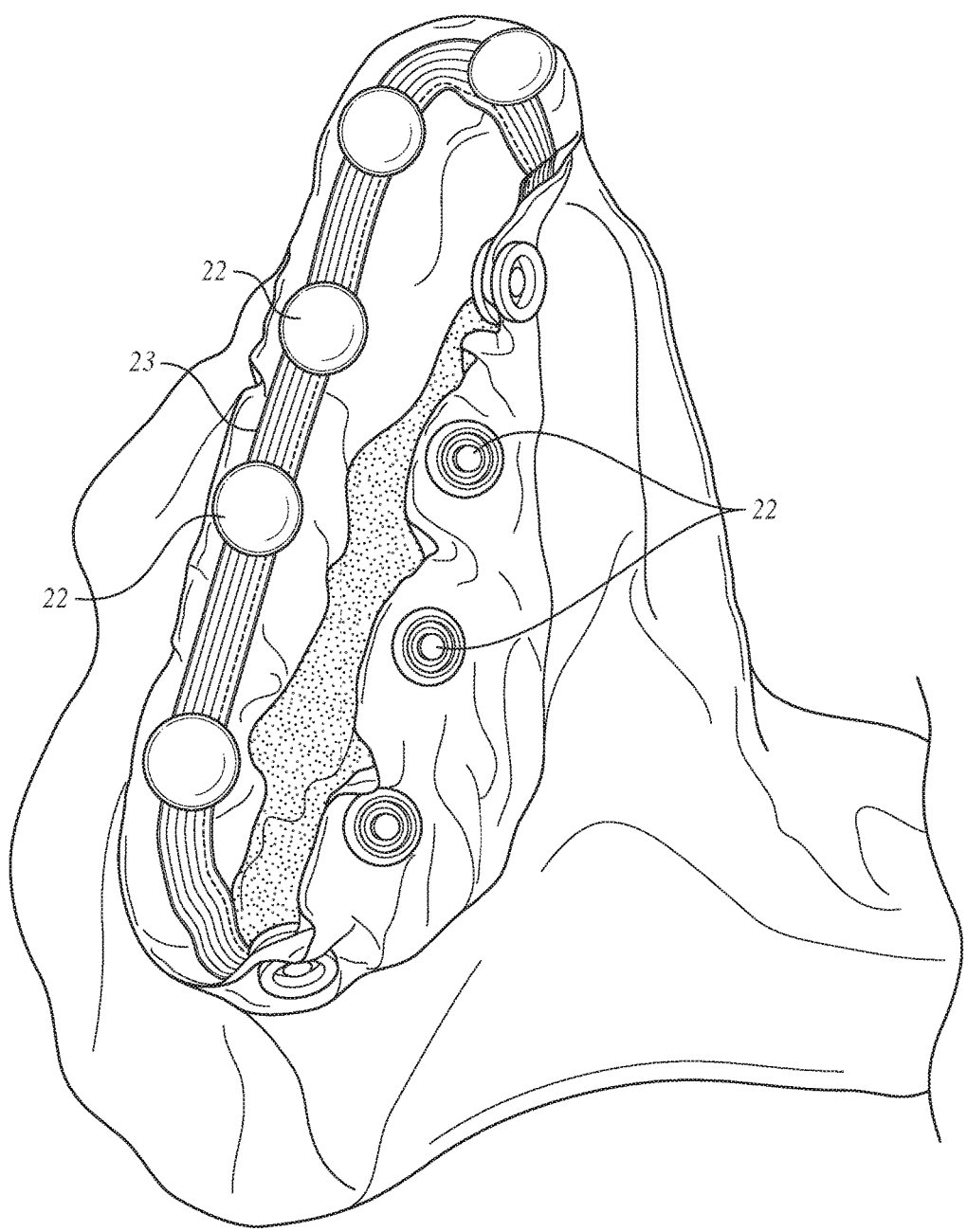
FIG. 7 is an isometric view of a hose seal in the open position accordance with FIG. 6 but turned in a manner to reveal an elastic band.
Figure 8:
FIG. 8 is an isometric view of a hose seal in a closed position in which the elastic seal and snaps are hidden from view.

The unsealed area 1 and 6 of FIG. 1, the side openings 13A, 13B of FIGS. 2-5, the bottom openings 14A, 14B of FIGS. 2 and 3 and the bottom opening 14 of FIGS. 4-5 each constitute an "access area" when open for the introduction of pressurized conditioned air via an air hose from a source of such pressurized conditioned air. The open position of the access area is shown in FIGS. 6 and 7 and the closed position of the access area is shown in FIG. 8.

That is, the "access area" is opened to form an opening 21 by unsnapping snaps 22 to gain access to the flow areas 7 of FIGS. 1-5. An air discharge end of an air hose may be inserted into the opening 21. An elastic band 23, which is secured to the bed covering or blanket about the periphery of the opening 21, may be stretched about the hose to help retain and create a seal around the air hose in its inserted position for discharging air into the flow areas 7.

The opening 21 may be closed by snapping closed the snaps 22. Once the snaps 22 are closed, the snaps 22 and the elastic band 23 act such that they cannot be seen exteriorly as depicted in FIG. 8. Instead, all that can be seen is a fold line 25 that forms from the blanket fabric as a result of the closed snaps.

Figure 9:
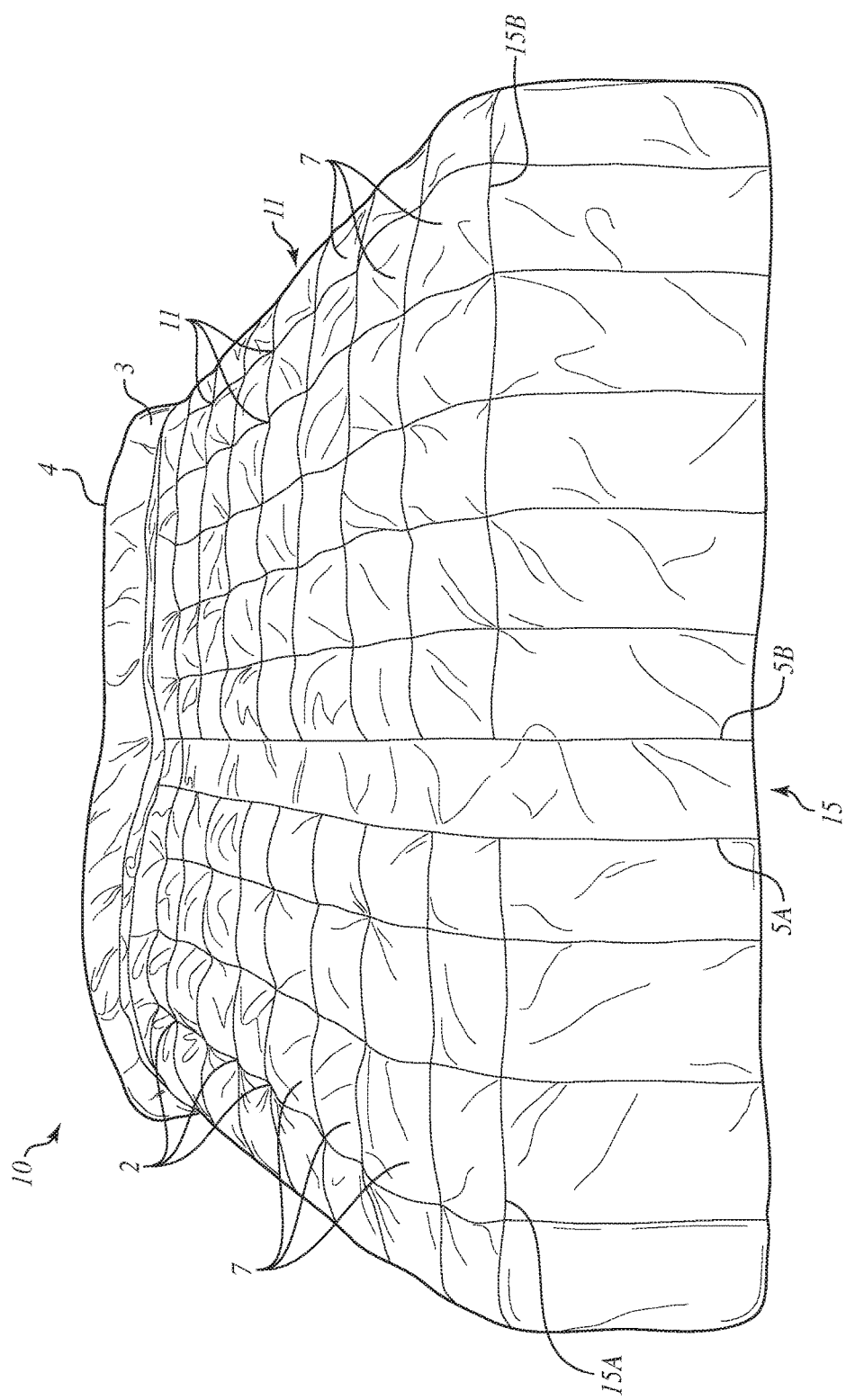
FIG. 9 is an isometric view of the further blanket of FIGS. 2 and 3 after inflation of the blanket.

Indeed, the user is given a choice of using either a side opening (1, 6, 13A, 13B of FIGS. 1-5 as applicable) or a bottom opening (14, 14A, 14B of FIGS. 2-5 as applicable) for the air hose. The side or bottom openings that are not used for the air hose, therefore, may be closed by snapping closed the snaps 22, thereby hiding the elastic band 23 and the snaps 22 from view in the manner of FIG. 8. This hidden opening appearance is strongly preferred for the multiple redundant access areas that may not be used. The result from inflation of the bed covering or blanket is shown in FIG. 9. As can appreciated, the location of the tack stitches 2 in a uniform manner prevents giving rise to a ballooning effect.

Figure 10:
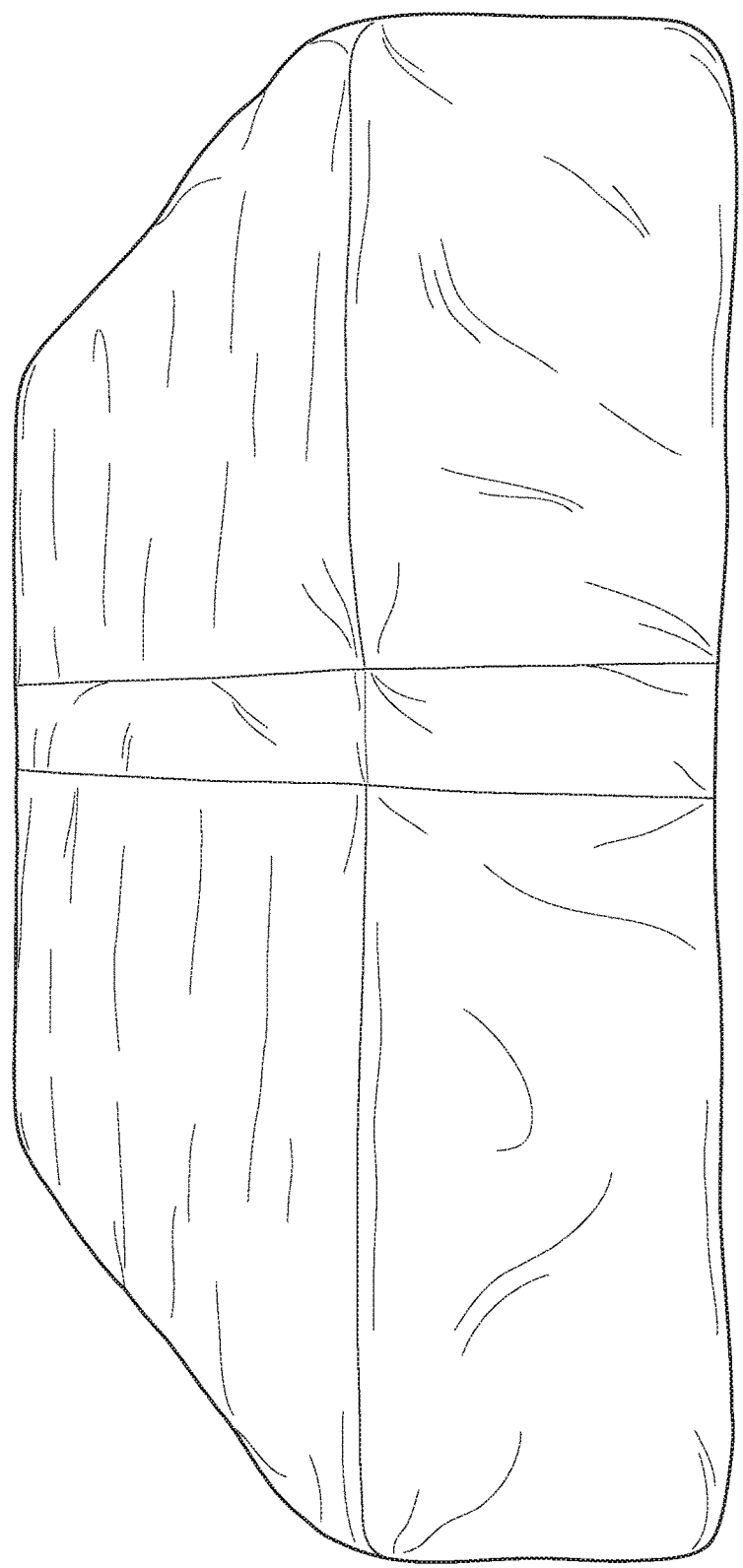
FIGS. 10 and 11 show a blanket before and after inflation, respectively.
Figure 11:
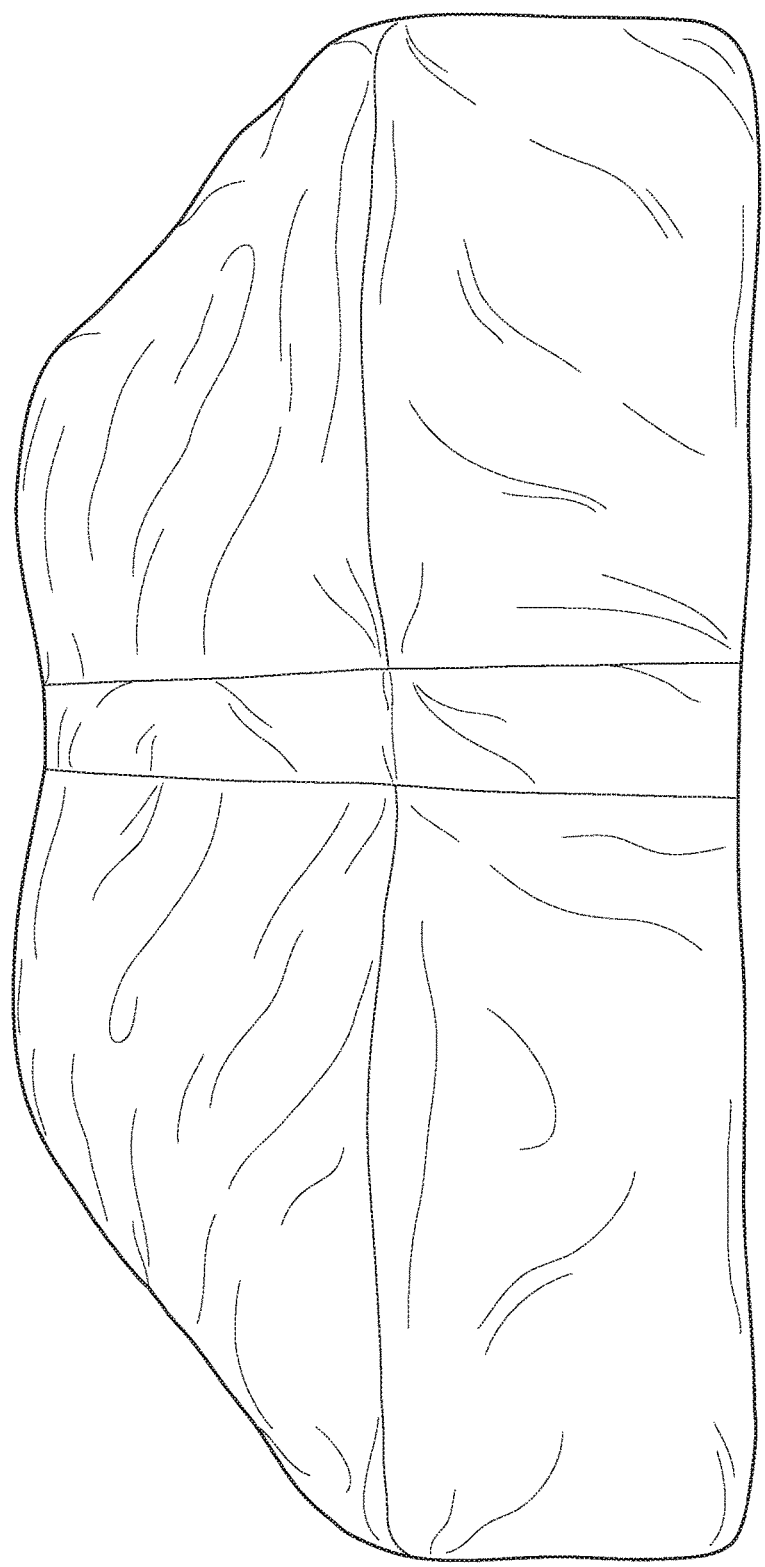

Turning to FIGS. 10 and 11, a simple sheet assembly with an interior air cavity is shown before and after its inflation, respectively. Indeed, the bed covering in FIG. 11 could be even more "balloony" than shown. Unlike the embodiments of the invention, there are no uniformly spaced apart joining means, such as thread stitches, to join together the plurality of sheets that comprising the bed covering. The presence of the thread stitches 2 of FIGS. 1-5 and 9 arranged in the uniform manner throughout the central region of the bed covering prevents the full ballooning effect of FIG. 11 from arising. The absence of such thread stitches, as in the bed covering of FIGS. 10 and 11, enables the ballooning effect to arise upon inflation of the internal airflow cavity. In practice this ballooning could result in a vertical inflation of more than 18 inches, which is very undesirable.

While the foregoing description and drawings represent the preferred embodiments of the present invention, it will be understood that various changes and modifications may be made without departing from the scope of the present invention.

What is claimed is:

1. A bed covering apparatus for receiving and distributing a pressurized airflow, the apparatus comprising: a bedding material that is flexible to overlay a bed, the bedding material having at least one zone, the at least one zone having an associated region and an at least one associated inlet, the at least one associated inlet being arranged to channel airflow into the associated region, the bedding material including a plurality of layers in contact with each other in a one over the other relation to form at least one internal air cavity between the plurality of layers, the plurality of sheet layers including an upper layer and a lower layer; and a plurality of joining elements that join together the plurality of layers to each other at a plurality of spaced apart locations so as to suppress a ballooning effect that would otherwise arise from inflation by pressurized air wherein the plurality of joining elements include three of the joining elements within confines of any given area of quadrilateral shape having all right angles within the associated region, the given area being spaced away from the at least one air inlet, the bedding material having a further area closer than the given area is to the at least one associated inlet and that is of an identical dimension and same relative orientation to that of the given area, the further area lacking any of the joining elements, the further region extending from the at least one associated inlet.

2. The apparatus in claim 1, further comprising: a middle layer that is of smaller size than the lower layer and arranged between the lower layer and the upper layer.

3. The apparatus in claim 1, wherein the upper and lower layers are woven layers, the bedding material also including a thermal layer that has a higher thermal insulating characteristic than the woven layers, at least one of the woven layers being sewn onto the thermal layer, the joining elements being thread stitches, the bedding material being a blanket.

4. The apparatus in claim 1, wherein the at least one internal airflow cavity includes two separate internal airflow cavities, the at least one air inlet includes two separate air inlets within respective ones of dual zones of the bedding material wherein the two separate air inlets communicate with respective ones of the two separate internal air cavities for delivery of the pressurized air therein.

5. The apparatus in claim 4, wherein the pressurized air within at least one of the two separate internal airflow cavities is in a heated condition at a temperature higher than that of ambient temperature and the pressurized air within a remaining one of the two separate internal airflow cavities is at the ambient or cooled temperature.

6. The apparatus in claim 1, wherein the pressurized air within the at least one internal airflow cavity is in a heated condition that is at a higher temperature than that of ambient temperature.

7. The apparatus in claim 1, wherein the pressurized air within the at least one internal airflow cavity is at ambient or cooled temperature.

8. The apparatus in claim 1, wherein the bedding material has a center area and has end regions, the center area separating the end regions from each other, further comprising: means for sealing the center area from each of the end regions so that each of the end regions remain in a non-inflated state despite the center area being in an inflated state from the delivery of the pressurized air into the at least one internal airflow cavity.

9. The apparatus in claim 1, wherein the at least one air inlet is formed from portions of the plurality of layers and bounded by snaps, the snaps being arranged to snap closed and become hidden from view within folds of the plurality of layers.

10. The bed covering apparatus in claim 9, wherein the at least one air inlet is also bounded by an elastic band in addition to being bounded by the snaps, the snaps being arranged in a manner relative to the elastic band so that the elastic band and the snaps become hidden from view within folds of the woven layers with the snaps closed.

11. The apparatus in claim 1, further comprising: multiple redundant air inlet sections at edges in the bedding material that are configured to be alternately sealed and unsealed.

12. The bed covering apparatus in claim 1, wherein the layers are woven and arranged in a one over another relation with the upper layer having a tighter weave than that of the lower layer so that air permeability through the lower layer is higher than that for the upper layer.

13. The bed covering apparatus in claim 12, wherein the lower layer has no visible holes, slits or apertures that would tend to increase air permeability beyond that of the weave of material of the lower layer.

14. A method for receiving and distributing a pressurized airflow in a bed covering apparatus the method comprising: providing a bedding material that is flexible to overlay a bed, the bedding material having at least one zone, the at least one zone having an associated region and at least one associated air inlet, the associated at least one air inlet being arranged to channel airflow into the associated region, the bedding material including a plurality of layers in contact with each other in a one over the other relation to form at least one internal air cavity between the plurality of layers, the plurality of layers including an upper layer and a lower layer; and arranging a plurality of joining elements to join together the plurality of layers to each other at a plurality of spaced apart locations to suppress a ballooning effect that would otherwise arise from inflation by pressurized air, wherein the plurality of joining elements include three of the joining elements within confines of any given area of quadrilateral shape having all right angles within the associated region, the given area being spaced away from the at least one air inlet, the bedding material having a further area closer than the given area is to the at least one associated inlet and that is of an identical dimension and same relative orientation to that of the given area, the further area lacking any of the joining elements, the further region extending from the at least one associated inlet.

15. The method in claim 14, further comprising: a middle layer that is of smaller size than the lower layer and sewn to the lower layer and arranged between the lower layer and the upper layer with the air inlet spaced above the middle layer.

16. The method in claim 14, further comprising: providing the bedding material with a higher thermal insulating characteristic than that of the plurality of layers by including a thermal layer sewn to at least one of the plurality of layers, the joining elements being thread stitches, the bedding material being a blanket.

17. The method in claim 14, wherein the at least one associated air inlet includes two separate air inlets, further comprising: delivering the pressurized air into respective ones of the two separate internal airflow cavities, the two separate air inlets being in fluid communication with respective ones of two separate internal airflow cavities.

18. The method in claim 17, wherein the pressurized air within at least one of the two separate internal airflow cavities is in a heated condition at a higher temperature than that of ambient temperature and the pressurized air within at least another of the two separate internal airflow cavities is at the ambient or cooled temperature.

19. The method in claim 14, wherein the pressurized air within the at least one internal airflow cavity is in a heated condition that is at a higher temperature than that of ambient temperature.

20. The method in claim 14, wherein the pressurized air within the at least one internal airflow cavity is at ambient or cooled temperature.

21. The method in claim 14, wherein the bedding material has a center area and opposite end regions, the center area separating the opposite end regions from each other, further comprising: sealing the center area from each of the opposite end regions so that each of the opposite end regions remain in a non-inflated state despite the center area being in an inflated state from the delivery of the pressurized air into the at least one internal airflow cavity.

22. The method in claim 14, further comprising: forming the at least one air inlet from portions of the plurality of layers and bounded by an elastic band and snaps, the snaps being arranged to snap closed so that the elastic band and the snaps become hidden from view within folds of the plurality of layers.

23. The method in claim 14, further comprising: providing multiple redundant air inlet sections at edges in the bedding material that are configured to be sealed and unsealed as needed.

24. The method in claim 14, wherein the bedding material has two sides and two ends, the at least one air inlet including two inlets; further comprising: arranging one of the two inlets at one of the ends of the bedding material and another of the two inlets at one of the sides of the bedding material, the two inlets being in fluid communication with the at least one internal airflow cavity.

25. The method in claim 14, wherein the layers are woven, further comprising: arranging the layers in a one over another relation with the upper layer having a tighter weave than that of the lower layer so that air permeability through the lower layer is higher than that for the upper layer.

26. The method in claim 25, further comprising: providing the lower layer free of visible holes, slits or apertures that would tend to increase air permeability beyond that of the weave of material of the lower layer.

27. A bed covering apparatus, comprising: a bedding-material made of layers of flexible material to overlay a bed, the bedding material being configured into dual zones, each of the dual zones having an associated region and at least one associated inlet, the at least one associated inlet being arranged to channel airflow into one of the associated region, each of the associated regions of the dual zones having a plurality of joining elements that join together an upper layer of the bedding material and a lower layer of the bedding material, wherein the plurality of joining elements include three of the joining elements within confines of any given area of quadrilateral shape having all right angles within the associated region, which is spaced away from the at least one associated inlet, the bedding covering having a further area closer than the given area is to the at least one associated inlet and that is of an identical dimension and same relative orientation to that of the given area, the further area lacking any of the joining elements, the further region extending from the at least one associated inlet.

28. The bed covering apparatus in claim 27, further comprising: two airflow sources, one of the two airflow sources being a source of ventilated air, another of the two airflow sources being a source of tempered air that is heated to a temperature higher than that of the ventilated air.

29. The apparatus in claim 27, wherein the upper and lower layers are woven and arranged in a one over another relation with the upper layer having a tighter weave than that of the lower layer so that air permeability through the lower layers is higher than that for the upper layer.

30. The apparatus in claim 29, wherein the lower layer has no visible holes, slits or apertures that would tend to increase air permeability beyond that of the weave of material of the lower layer.

* * * * *